United States Patent

Whitlock et al.

Patent Number: 5,628,750
Date of Patent: May 13, 1997

[54] TIBIAL RESECTION GUIDE ALIGNMENT APPARATUS AND METHOD

[75] Inventors: Steven I. Whitlock, Austin; Mark L. Rehmann, Pflugerville, both of Tex.

[73] Assignee: U.S. Medical Products, Inc., Austin, Tex.

[21] Appl. No.: 496,980

[22] Filed: Jun. 30, 1995

[51] Int. Cl.$^6$ .................................................. A61B 17/56
[52] U.S. Cl. ................................. 606/88; 606/86; 606/87
[58] Field of Search ............................... 606/80, 82, 86, 606/87, 88, 96, 102

[56] References Cited

U.S. PATENT DOCUMENTS

| | | |
|---|---|---|
| 4,841,975 | 6/1989 | Woolson ........................ 128/653 |
| 4,952,213 | 8/1990 | Bowman et al. ................. 606/79 |
| 5,342,368 | 8/1994 | Peterson ........................ 606/88 |
| 5,395,377 | 3/1995 | Peterson et al. ................. 606/88 |

OTHER PUBLICATIONS

Zimmer Adjustable Tibial Resector, 1992.
PFC Modular Total Knee System, 1990, pp. 18–27.
Surgical Technique with the Howmedia Universal Knee Instruments, pp. 15–21.
The Continuum Knee System Surgical Technique, pp. 9–10.
The Intermedics Natural–Knee System, 1992, pp. 14–19.

*Primary Examiner*—Guy V. Tucker
*Assistant Examiner*—David O. Reip
*Attorney, Agent, or Firm*—Shaffer & Culbertson; Russell D. Culbertson

[57] ABSTRACT

A tibial resection guide alignment apparatus (10) includes an elongated base member (12) and structure connected to the base member for connecting the base member about a patient's tibia in an operating position adjacent to the anterior side of the surgically exposed tibial plateau. When connected in the operating position, a depth adjustment axis (D) associated with the base member (12) extends substantially parallel to the longitudinal axis of the patient's tibia. A carriage member (16) is slideably mounted on the elongated base member (12) so that its position may be adjusted along the depth adjustment axis. A depth adjustment mechanism (22) associated with the base member (12) and carriage member (16) provides fine adjustment to position the carriage member along the depth adjustment axis and then fix the carriage member in a desired position along the depth adjustment axis. A guide block mount (20) is pivotally connected to the carriage member (16) so as to pivot about a slope adjustment axis (S) that extends substantially perpendicular to the depth adjustment axis (D) and a slope adjustment mechanism (24) is associated with the carriage member. The slope adjustment mechanism (24) operates to pivot the guide block mount (20) about the slope adjustment axis (S) and to fix the guide block mount (20) in a desired orientation about the slope adjustment axis (S). Also, a guide block connecting arrangement is associated with the guide block mount (20) for releaseably securing a tibial resection guide (28) to the guide block mount (20). The connection for securing the base member (12) to the patient's tibia may be intermedullary or extramedullary since all of the adjustment for posterior/anterior slope and depth are provided on the alignment apparatus (10) adjacent to the proximal end of the tibia.

13 Claims, 5 Drawing Sheets

Fig. 5 in the cut.
TIBIAL RESECTION GUIDE ALIGNMENT APPARATUS AND METHOD

BACKGROUND OF THE INVENTION

This invention relates to total knee replacement or arthroplasty and particularly to an alignment apparatus and method for aligning a resection guide used in resecting the tibial plateau.

In total knee replacement or arthroplasty, the proximal surface of the tibia is removed or resetted and an implant affixed over the resected surface. The implant includes artificial articulating surfaces to replace the natural articulating surfaces which have been removed. The resection of the proximal surfaces of the tibia must leave a surface having a specific posterior slope and varus/valgus angle that are unique to every patient. Also the depth of the cut must be specifically tailored for the thickness of the implant in order to properly position the artificial articulating surfaces.

Due to the critical nature of the cut required through the tibial plateau, a saw guide block or resection guide is preferably fixed to the tibia and used to guide a saw blade in making the cut. The resection guide includes a planar guide surface that guides the saw blade in the appropriate plane to produce the desired resected surface. The resection guide itself must be aligned with its planar guide surface in the plane necessary to provide the desired cut, and alignment devices have been developed to align the resection guide with respect to the surgically exposed tibia. Using the alignment instrument, the resection guide is aligned primarily to match natural landmarks of the tibial plateau and lower leg.

The alignment devices include means for adjusting the posterior/anterior slope of the resection guide, the depth of the resection guide's guide surface below the top of the tibia, and the varus/valgus or lateral/medial slope. Tibial resection guide alignment devices fall into two broad categories, extramedullary mounted devices and intramedullary mounted devices. The extramedullary devices are connected outside the patient's tibia while the intramedullary alignment devices include an intramedullary rod that is positioned down the central canal of the tibia and the alignment mechanism suspended from the rod. In either type of alignment device, the resection guide was first attached to the device, the device was connected to the patient, and then the alignment device was operated to provide the desired alignment. Once the resection guide was aligned, it was temporarily fixed in place on the anterior side of the tibia and the alignment device removed to allow the cutting or resection operation.

An intramedullary or extramedullary mount is generally a matter of preference for the particular surgeon. Prior alignment guides were restricted to one type of mount, either intramedullary or extramedullary. Therefore, to meet surgeon preference, two sets of tools had to be available. Furthermore, the prior intramedullary mounted alignment guides did not provide fine adjustments for cutting depth and slope.

SUMMARY OF THE INVENTION

It is a general object of the invention to provide a tibial resection guide alignment apparatus and method that overcomes the above problems and others associated with prior alignment devices. More particularly, it is an object of the invention to provide a tibial resection guide alignment apparatus that may be mounted both extramedullar or intramedullar. Another object of the invention is to provide a tibial resection guide alignment apparatus that includes an intramedullary mounting arrangement and still provides for fine depth and slope adjustments.

In order to accomplish these objects, the apparatus according to the invention provides both fine slope and depth adjustment mechanisms adjacent to a guide block mount upon which the resection guide is mounted for alignment. The position of the fine adjustment mechanisms near the guide block mount allow the device to be supported by an intramedullary rod or extramedullary mounting arrangement and still provide the desired fine adjustment. The varus/valgus adjustment mechanism is removed from the area of the guide block mount at the end of the extramedullary mounting device and therefore fine varus/valgus adjustment is available only with the extramedullary mount associated with the device.

The apparatus includes an elongated base member with a carriage member slideably mounted on the base member along a depth adjustment axis. A depth adjustment mechanism associated with the carriage may be operated to move the carriage along the depth adjustment axis and fix the carriage at a desired position along the axis. A guide block mount to which the resection guide is removably connected is pivotally connected to the carriage so that it may pivot about a slope adjustment axis extending perpendicular to the depth adjustment axis. A slope adjustment mechanism is associated with the carriage and may be operated to pivot the guide block mount about the slope adjustment axis and thereby adjust posterior/anterior slope, and to fix the guide block mount in the desired position about the axis.

With the posterior/anterior slope adjustment and depth adjustment mechanisms both associated with the base member, the base member may be connected to the patient's tibia through either an intramedullary mount or an extramedullary mount and provide the two fine adjustments. With either the intramedullary or extramedullary mount, the alignment device includes an arm connected to the base member in a position to extend over the surgically exposed proximal end of the tibia. The arm includes an opening for receiving an intramedullary rod and also includes members for gripping the proximal end of the tibia. The extramedullary mount includes a separate extramedullary member which may be removably connected to the base member, and a bottom assembly connected to the extramedullary member by which the device may be connected around the patient's lower leg or ankle. Varus/valgus adjustment is provided in the connection between the extramedullary member and the bottom assembly.

The preferred form of the invention includes both a depth stylus and a slope stylus that may be connected to the guide block mount or resection guide itself. The slope stylus includes an elongated slope stylus member preferably lying in the plane of the planar guide surface on the resection guide when the guide is properly connected to the guide block mount. An extension member positions the slope stylus member adjacent to the tibial plateau so that the stylus member provides a visual indication for comparison to the natural posterior/anterior tibial slope. The depth stylus member includes a stylus end that terminates in a plane parallel to the planar guide surface of the resection guide and spaced above such guide plane a distance equal to the thickness of the prosthesis to be implanted.

These and other objects, advantages, and features of the invention will be apparent from the following description of the preferred embodiments, considered along with the accompanying drawings.

DESCRIPTION OF THE PREFERRED EMBODIMENTS

Figure 1:
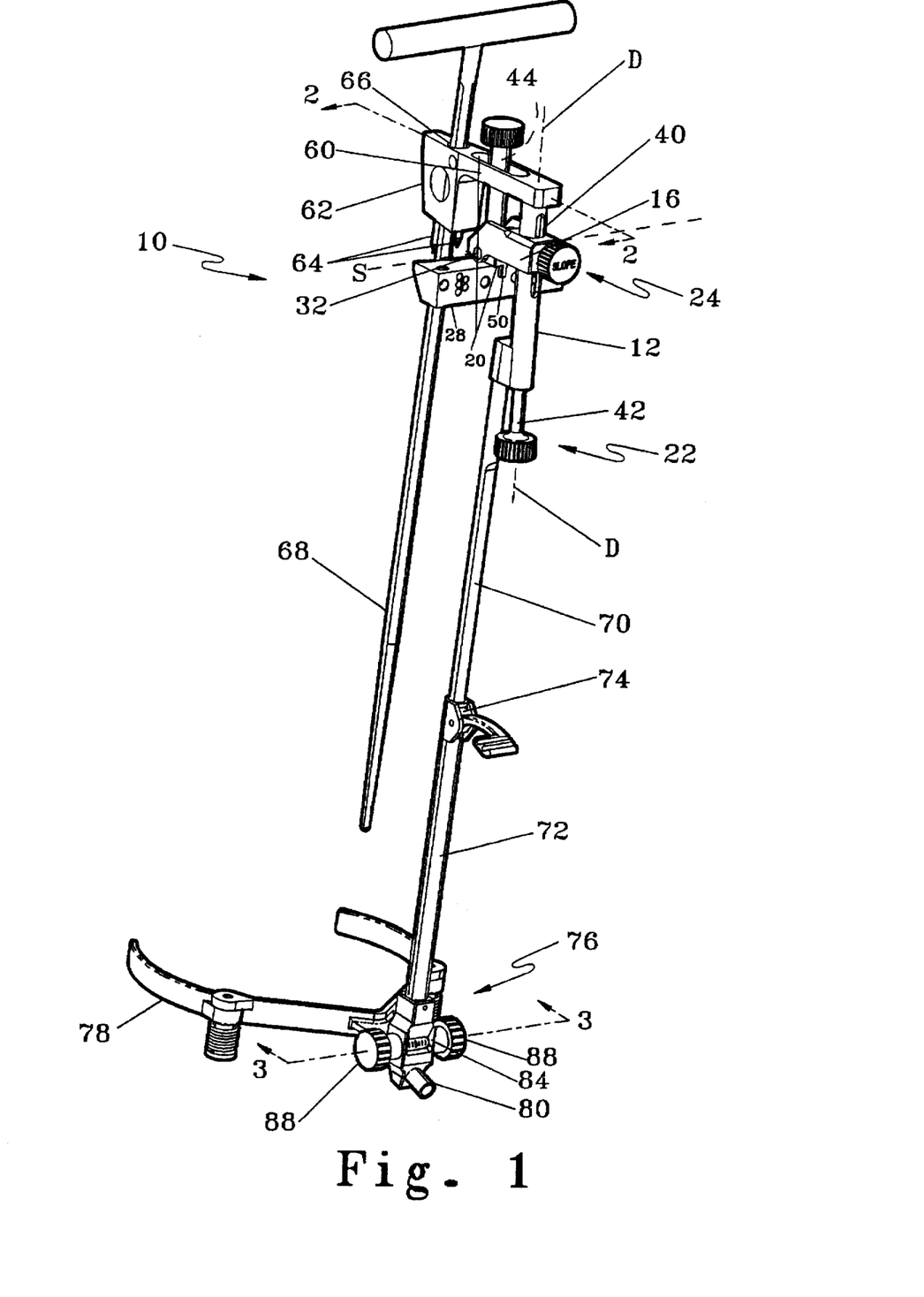
FIG. 1 is isometric drawing showing a tibial resection guide alignment apparatus embodying the principles of the invention.
Figure 2:
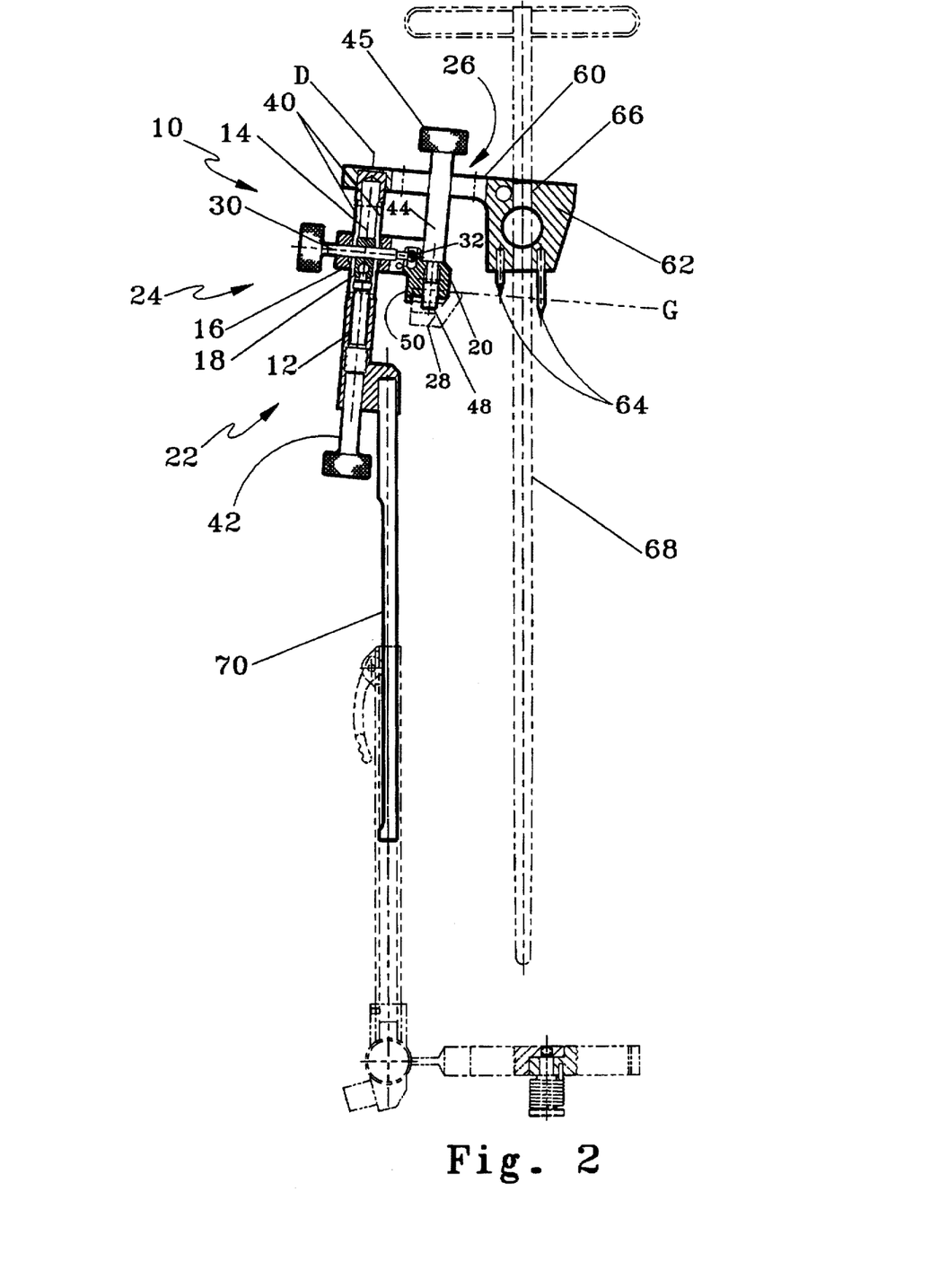
FIG. 2 is a partial longitudinal section view taken along line 2—2 in FIG. 1.

FIGS. 1 and 2 show the tibial resection guide alignment apparatus 10 including a base member 12 having a base opening 14 extending along its length along a depth adjustment axis D. A carriage member 16 is slideably received over the base member 12. The apparatus 10 also includes a guide block mount 20 pivotally connected to the carriage 16 so as to pivot about a slope adjustment axis S extending perpendicular to the depth adjustment axis D. The base member 12 also has associated with it depth adjustment means 22 for positioning the carriage along the depth adjustment axis D, and slope adjustment means 24 for positioning the guide block mount about the slope adjustment axis S. Also, resection guide connecting means 26 associated with the guide block mount 20 allows a resection guide 28 (shown in phantom) to be connected to the guide block mount for alignment.

The slope adjustment means 24 includes the nut 18 received in the base opening 14 and a slope adjustment member 30 threaded through the carriage member 16 and the nut, and terminating in a pivot connection 32 to the guide block mount 20. The threaded slope adjustment member 30 may be threaded in and out through the carriage member 16 and nut 18 to force the guide block mount 20 to pivot about the slope adjustment axis S and provide fine posterior/anterior slope adjustment for the resection guide 28 connected to the guide block mount 20.

The depth adjustment means 22 includes slots 40 extending along a portion of the base member 12 through which the threaded slope adjustment member 30 passes, and a threaded depth adjustment member 42. The depth adjustment member 42 is threaded through the base opening 14 and rotateably connected at one end to the nut 18. The depth adjustment member 42 threads in and out through the base member 12 to provide fine depth adjustment by forcing the nut 18 through the base member opening 14 and along with the nut, the carriage member 16, threaded slope adjustment member 30, and the guide block mount 20.

The resection guide connecting means 26 includes a connecting member 44 extending through an opening through the guide block mount 20 and terminating in a threaded end section 48. The threaded end section 48 is adapted to cooperate with a female threaded opening on the resection guide 28. The resection guide 28 is connected to the guide block mount 20 in this form of the invention by aligning the resection guide on the bottom surface of the guide block mount and turning the threaded connecting member 44 to start the threaded end 48 into the female threaded opening on the resection guide 28 and draw the resection guide tightly against the bottom surface of the guide block mount 20. Also, the resection guide connecting means 26 preferably includes an alignment feature 50 formed on the bottom surface of the guide block mount 20. The alignment feature 50 registers with openings formed on the top of the resection guide 28 to allow the resection guide to be connected in only one position on the guide block mount 20 and ensure that the resection guide 28 is properly connected.

A connecting arm member 60 is connected to a top end of the base member 12. The connecting arm 60 extends in the direction in which the guide block mount 20 is separated from the base member 12 and includes an end section 62 which is adapted to extend over the top of a surgically exposed proximal end of a tibia when the base member is properly connected to the tibia in an operating position. A slot in the connecting arm 60 accepts the threaded connecting member 44 with a knurled end 45 of the threaded connecting member extending conveniently above the connecting arm. Preferably two or more engagement or spike members 64 extend downwardly from the end section 62 of the connecting arm 60 in position to be driven into the top of the proximal end of the tibia with the base member in the operating position extending downwardly along the anterior side of the tibia. Also, the connecting arm 60 includes an opening 66 extending through the arm end section 62 for receiving an intramedullary mounting rod 68 (shown in phantom).

To accommodate extramedullary mounting, the apparatus 10 also includes an extension member 70 connected to the base member 12 and extending downwardly from the base member in a plane defined substantially by the depth adjustment axis D and the connecting arm 60. The extramedullary mounting arrangement also includes an extramedullary mounting member 72 that may be removably connected to extension member 70 and locked in place with a suitable locking mechanism 74. The locking mechanism allows the overall length of the extramedullary mounting structure to be adjusted to the length of the tibia. A bottom assembly 76 extends at substantially a fight angle to the axis of the extramedullary mounting member 72 and includes a cradle assembly 78 for securing around the patient's ankle or lower leg. The bottom assembly 76 may also include a receptacle 80 extending in the opposite direction from the ankle cradle assembly 78 for receiving an alignment rod (not shown) which a physician may use in aligning the device 10 on a patient's tibia.

Figure 3:
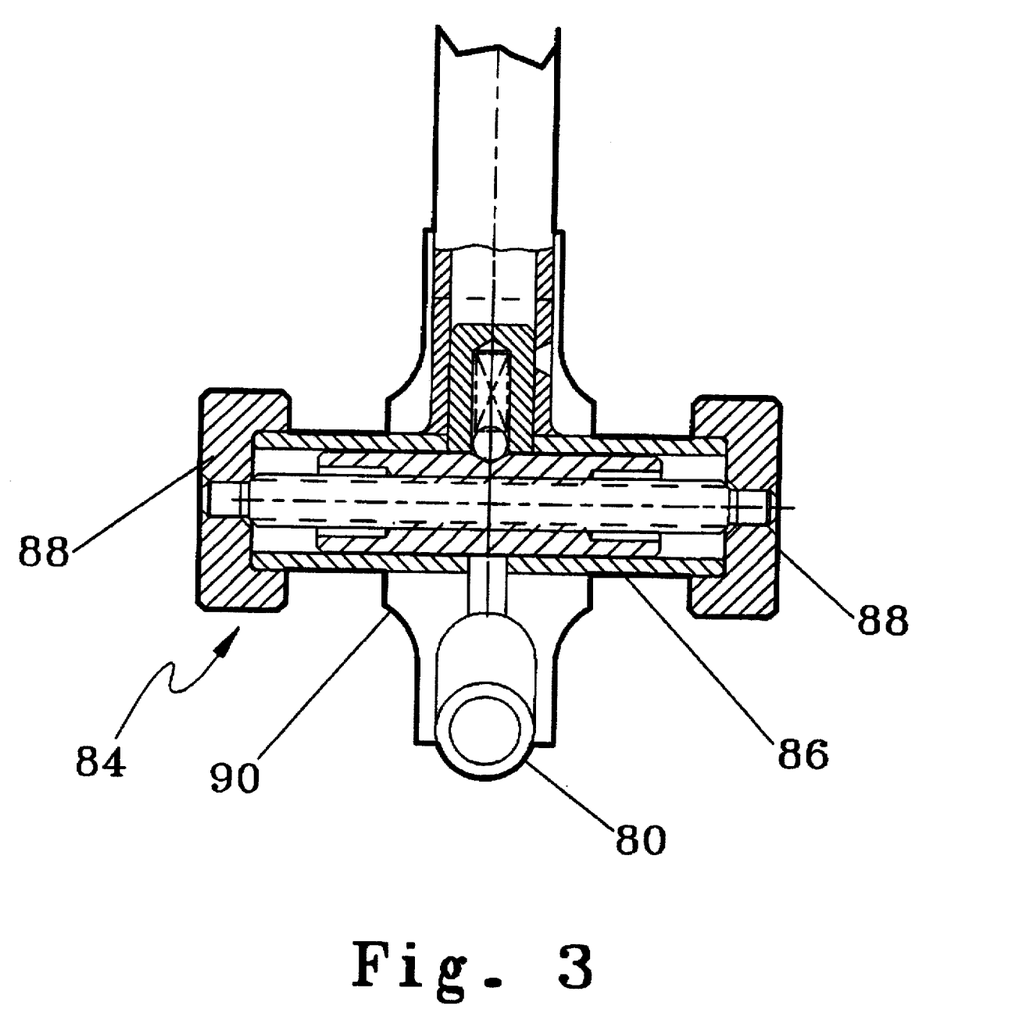
FIG. 3 is a view in section taken along line 3—3 through the varus/valgus adjustment mechanism.

Referring to FIGS. 1, 2, and 3, the preferred extramedullary mounting arrangement also includes varus/valgus adjusting means 84 associated with the bottom assembly 76 and the extramedullary mounting member 72. The varus/valgus adjusting mechanism 84 comprises a threaded adjustment member 86 connected to knurled knobs 88, and a slide device 90 that is threaded over the threaded adjustment member and is connected to the ankle cradle assembly 78. Turning the threaded adjustment member 86 using the knurled knobs 88 causes the threaded slide device 90 to move laterally along the threaded adjustment member 88 therefore moving the ankle cradle assembly laterally as well.

Figure 4:
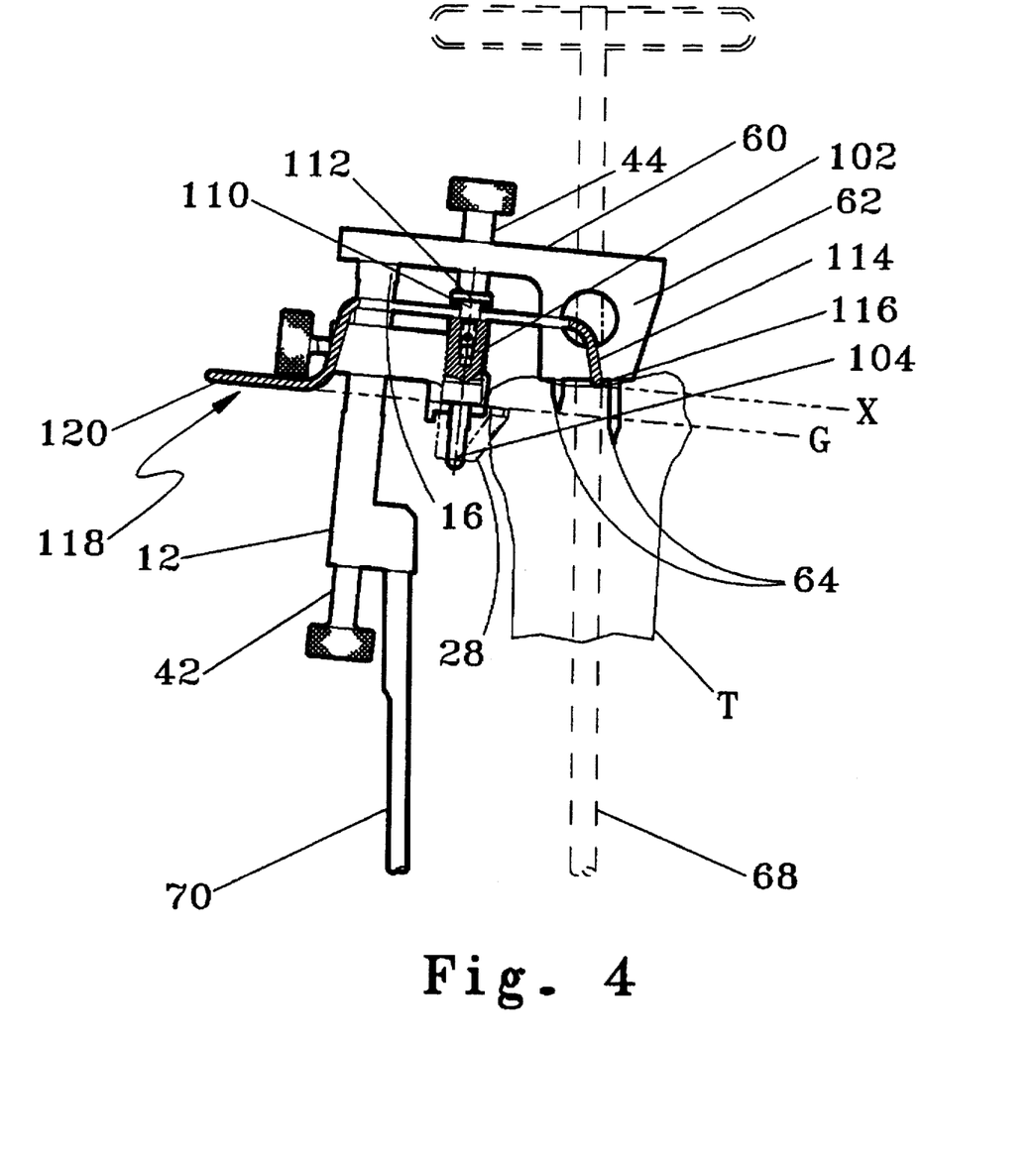
FIG. 4 is a partial longitudinal section view of the guide block mount with the depth stylus in position for providing a depth indication.
Figure 5:
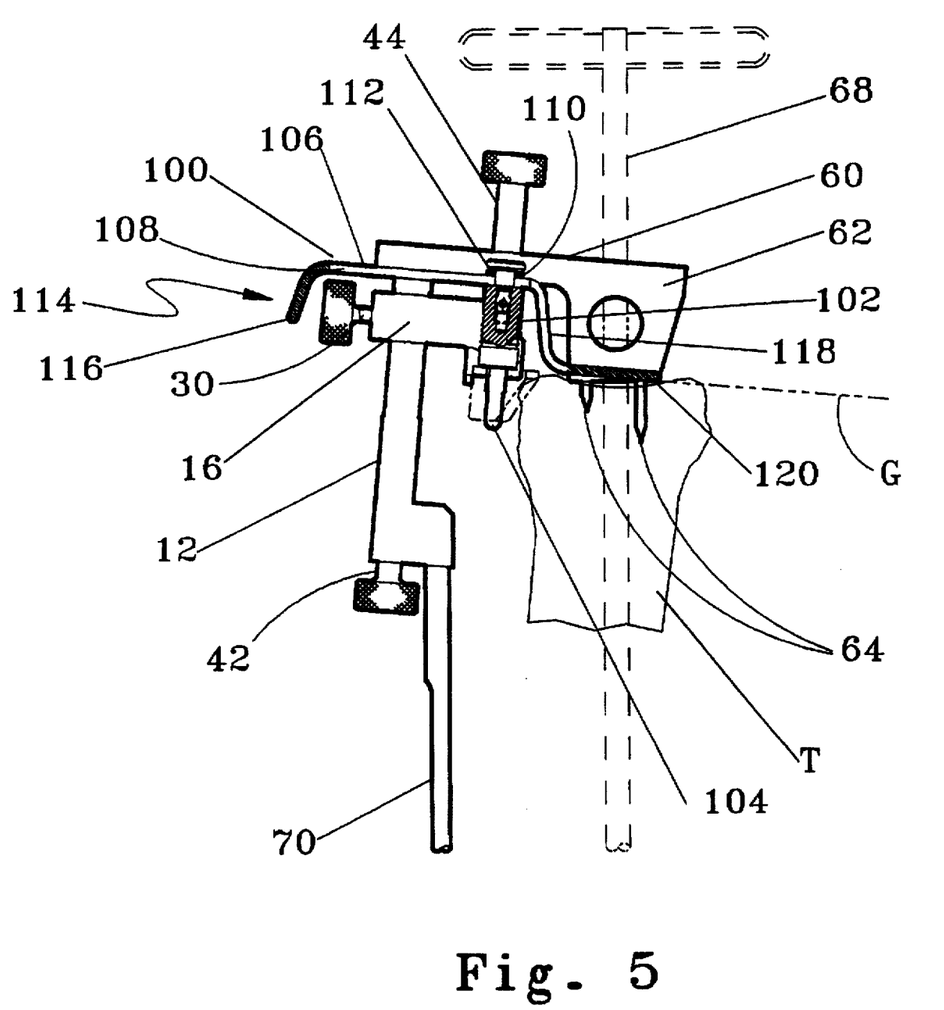
FIG. 5 is a partial longitudinal section view similar to FIG. 4 but showing the slope stylus in position for providing a visual indication of the guide slope.

Referring now to FIGS. 4 and 5, the apparatus preferably includes a combination depth stylus and slope stylus 100 that may be connected to the resection guide 28 through a stylus connecting member 102. The stylus connecting member 102 preferably includes an end section 104 adapted to extend into an opening through the resection guide 28. The preferred combined depth stylus and slope stylus 100 includes an elongated center section 106 having a slot 108 through which the device may be connected to the top of the stylus connecting member 102. The top of the stylus connecting member 102 includes a reduced diameter section 110 that may extend through the slot 108 with a cap member 112 threaded over the reduced diameter section 110 to fix the combined stylus 100 in the desired position. In addition to the central section 106 of the unitary stylus 100, the stylus includes a depth stylus section 114. The depth stylus section 114 has an end 116 that terminates in a depth plane extending parallel to the plane G of the resection guide 28 guide surface when the guide is properly connected on the guide block mount 20. The depth plane X is also separated from the plane G of the resection guide a distance equal to an implant thickness. The opposite end of the unitary stylus 100 includes a slope stylus section 118 terminating with an elongated slope member 120 that lies in the plane X defined by the guide surface of the resection guide 28 properly received on the guide block mount 20.

The operation of the apparatus 10 and the method of the invention may now be described with reference to FIGS. 1–5. First, the resection guide 28 is connected in position on the guide block mount 20 using the connecting member 44. With the resection guide 28 in place, the apparatus 10 is positioned with the end 62 of the connecting arm 60 extending over the surgically exposed proximal end of the patient's tibia T (FIGS. 4 and 5) and with the base member 12 extending downwardly on the anterior side of the tibia. With the base member 12 properly centered in front of the tibia, the connecting arm end section 62 is driven downwardly driving the spikes 64 into the proximal end of the tibia. At this point, the intramedullary rod 68 is inserted through opening 66 or the extramedullary mounting member 72 is attached over the rod 70 extending from the base member 12. Either mounting method stabilizes the base member 12 in front of the tibia T where the fine posterior/anterior slope adjustment and depth adjustment can be made to properly align the resection guide 28.

With the base member 12 stabilized on the anterior side of the tibia T, the stylus 100 is rotated to position the elongated slope stylus member 120 over, or adjacent to, the tibial plateau and the threaded depth adjustment member 42 is rotated to position the slope stylus member 120 just above the tibia as shown in FIG. 5. With the elongated slope stylus member 120 adjacent to the tibial plateau, the slope adjustment member 30 may be threaded in or out to provide fine slope adjustment until the slope of the elongated slope stylus member 120 matches the slope of the natural tibial plateau. Once the slope is matched, the stylus 100 is rotated again to position the depth stylus section over the proximal end of the tibia as shown in FIG. 4. The threaded depth adjustment member 42 can then be turned to move the resection guide 28 and guide block mount 20 downwardly parallel to the depth adjustment axis D until the depth stylus end 116 contacts the proximal end of the tibia T. Both the slope and depth of the resection guide 28 is now set and the resection guide may be temporarily fixed by suitable means to the anterior side of the tibial plateau prior to releasing the guide 28 from the guide block 20 and removing the alignment apparatus 10.

Where the extramedullary mount is used, the apparatus 10 also provides a fine varus/valgus angle adjustment through the adjustment mechanism 84 associated with the bottom assembly 76 and the bottom of the extramedullary mounting member 72. By sliding the end of the extramedullary mounting member 72 connected to the bottom assembly 76 along an axis extending perpendicular to the mounting member, the lateral/medial or varus/valgus angle of the attached resection guide 28 may be adjusted. A rod (not shown) may be inserted in the receptacle 80 for providing an alignment reference for the varus/valgus adjustment.

The above described preferred embodiments are intended to illustrate the principles of the invention, but not to limit the scope of the invention. Various other embodiments and modifications to these preferred embodiments may be made by those skilled in the art without departing from the scope of the following claims. For example, the resection guide 28 may be secured to the guide block mount 20 by any arrangement that allows the guide 28 to be released readily for removing the apparatus 10. Also, the extramedullary mounting arrangement may include any suitable bottom assembly for providing the desired extramedullary connection. Further, the slope stylus and depth stylus may be separate devices rather than the unitary device shown in the figures. The slope stylus and depth stylus may, in any event, be mounted on the resection guide directly or on the guide block mount.

We claim:

1. An apparatus for aligning a tibial resection guide during knee arthroplasty, the apparatus comprising:

(a) an elongated base member;

(b) a carriage member slidably mounted on the elongated base member so as to slide along a depth adjustment axis of the elongated base member;

(c) depth adjustment means associated with the base member and carriage member for adjusting the position of the carriage member along the depth adjustment axis of the base member and fixing the carriage member in a desired position along the depth adjustment axis of the base member;

(d) a guide block mount pivotally connected to the carriage member so as to pivot about a slope adjustment axis that extends substantially perpendicular to the depth adjustment axis;

(e) slope adjustment means mounted on the carriage member for adjusting the orientation of the guide block mount about the slope adjustment axis and fixing the guide block mount in a desired orientation about the slope adjustment axis;

(f) guide connecting means associated with the guide block mount for releasably securing the tibial resection guide to the guide block mount;

(g) a connecting arm connected to an upper end of the base member so as to extend over the center of the tibial plateau when the base member is in an operating position adjacent to the anterior side of the surgically exposed tibial plateau, in which operating position the depth adjustment axis extends substantially parallel to the longitudinal axis of the patient's tibia;

(h) at least one engagement member extending from a lower surface of the connecting arm for engaging the proximal end of the tibia;

(i) an intramedullary shaft;

(j) an intramedullary shaft opening extending through the connecting arm for receiving the intramedullary shaft extending into the tibial canal when the base member is in the operating position;

(k) an elongated extramedullary mounting member;

(l) extramedullary mount connecting means associated with the base member and the elongated extramedullary mounting member for rigidly connecting the elongated extramedullary mounting member to a lower end of the base member such that the extramedullary mounting member extends along the anterior side of the patient's tibia when the base member is in the operating position; and (m) a bottom assembly connected to a lower end of the extramedullary mounting member opposite the end of the extramedullary mounting member connected to the base member, the bottom assembly for attaching around a lower portion of the patient's tibia and fixing the lower end of the extramedullary mounting member relative to the patient's tibia.

2. The apparatus of claim 1 wherein the extramedullary mount connecting means comprises:

(a) an elongated extension member extending from the lower end of the base member;

(b) a receptacle formed in the elongated extramedullary mounting member for receiving a lower end of the elongated extension member; and (c) a locking member pivotally connected to the elongated extramedullary mounting member and adapted to be pivoted to a locked position with the elongated extension member received in the extramedullary mounting member receptacle, in which locked position the locking member provides a frictional engagement with the elongated extension member to rigidly connect the extramedullary mounting member to the elongated extension member.

3. The apparatus of claim 1 further comprising:

(a) varus/valgus alignment means associated with the bottom assembly for enabling the bottom assembly to slide along a varus/valgus alignment axis that extends substantially perpendicular to a longitudinal axis of the extramedullary mounting member and for fixing the lower end of the extramedullary mounting member in a desired position along the varus/valgus alignment axis with respect to the bottom assembly.

4. The apparatus of claim 1 further comprising a receptacle mounted on the bottom assembly for receiving an alignment rod.

5. The apparatus of claim 1 further including:

(a) a depth stylus associated with the resection guide connected to the guide block mount, the depth stylus including an extension member extending over the proximal end of the tibia when the base member is in the operating position, and further including a stylus end terminating in a stylus depth plane extending parallel to a resection guide plane, the stylus depth plane also being separated from the resection guide plane toward the connecting arm a distance equal to the thickness of a tibial implant.

6. The apparatus of claim 1 further including:

(a) a slope stylus associated with the resection guide connected to the guide block mount, the slope stylus including an extension member extending over the proximal end of the tibia when the base member is in the operating position, and further including an elongated slope member lying in a plane extending parallel to a guide plane associated with the resection guide.

7. The apparatus of claim 1 wherein the guide connecting means comprises:

(a) an elongated connecting member mounted on the guide block mount for rotation about the connecting member's longitudinal axis, the connecting member having a threaded end section adapted to cooperate with a threaded female receptacle on the resection guide to secure the guide to the guide block mount; and (b) a guide feature extending from a lower surface of the guide block mount for registering with a recess formed on the resection guide when the resection guide is connected to the guide block mount.

8. An apparatus for aligning a tibial resection guide during knee arthroplasty, the apparatus comprising:

(a) an elongated base member;

(b) a carriage member slidably mounted on the elongated base member so as to slide along a depth adjustment axis of the elongated base member;

(c) depth adjustment means associated with the base member and carriage member for adjusting the position of the carriage member along the depth adjustment axis of the base member and fixing the carriage member in a desired position along the depth adjustment axis of the base member;

(d) a guide block mount pivotally connected to the carriage member so as to pivot about a slope adjustment axis that extends substantially perpendicular to the depth adjustment axis;

(e) slope adjustment means mounted on the carriage member for adjusting the orientation of the guide block mount about the slope adjustment axis and fixing the guide block mount in a desired orientation about the slope axis;

(f) guide connecting means associated with the guide block mount for releasably securing the tibial resection guide to the guide block mount;

(g) tibia connecting means for connecting the base member to a patient's tibia with the base member in an operating position adjacent to the anterior side of the surgically exposed tibial plateau, in which operating position the depth adjustment axis extends substantially parallel to the longitudinal axis of the patient's tibia; and (h) a slope stylus associated with the tibial resection guide connected to the guide block mount, the slope stylus including an extension member and an elongated slope member lying in a plane extending parallel to a guide plane associated with the resection guide, the elongated slope member extending over, and adjacent to, a central portion of the proximal end of the tibia when the base member is in the operating position and the slope stylus is in a slope determining position.

9. The apparatus of claim 8 further including:

(a) a depth stylus associated with the tibial resection guide, the depth stylus including an extension member extending over the proximal end of the tibia when the base member is in the operating position and the depth stylus in a depth determining position, and further including a stylus end terminating in a stylus depth plane extending parallel to a resection guide plane, the stylus depth plane also being separated from the resection guide plane toward the connecting arm a distance equal to the thickness of a tibial implant.

10. The apparatus of claim 9 wherein the extension member of the depth stylus and the extension member of the slope stylus comprise a single elongated stylus extension member, and further including:

(a) a pivot connector connected to the elongated stylus extension member for connecting the elongated stylus extension member to the tibial resection guide so that the elongated stylus extension member may pivot to alternatively position either the depth stylus in the depth determining position or the slope stylus in the slope determining position.

11. An apparatus for aligning a tibial resection guide during knee arthroplasty, the apparatus comprising:

(a) an elongated base member;

(b) a carriage member slidably mounted on the elongated base member so as to slide along a depth adjustment axis of the elongated base member;

(c) depth adjustment means associated with the base member and carriage member for adjusting the position of the carriage member along the depth adjustment axis of the base member and fixing the carriage member in a desired position along the depth adjustment axis of the base member;

(d) a guide block mount pivotally connected to the carriage member so as to pivot about a slope adjustment axis that extends substantially perpendicular to the depth adjustment axis;

(e) slope adjustment means mounted on the carriage member for adjusting the orientation of the guide block mount about the slope adjustment axis and fixing the guide block mount at any orientation within a desired orientation range about the slope axis, the slope adjustment means comprising an elongated slop adjustment member mounted on the carriage member, the slope adjustment member having a first end pivotally connected to an arm of the guide block mount at a point removed from the slope adjustment axis, and an adjustment thread associated with the slope adjustment member for extending and retracting the first end of the slope adjustment member with respect to the carriage member as the slope adjustment member is rotated about its longitudinal axis;

(f) guide connecting means associated with the guide block mount for releasably securing the tibial resection guide to the guide block mount; and (g) tibia connecting means for connecting the base member to a patient's tibia with the base member in an operating position adjacent to the anterior side of the surgically exposed tibial plateau, in which operating position the depth adjustment axis extends substantially parallel to the longitudinal axis of the patient's tibia.

12. A method for aligning a tibial resection guide during arthroplasty, the method comprising the steps of:

(a) fixing the resection guide to a guide block mount connected to an elongated base member;

(b) mounting the base member in an operating position adjacent to the anterior side of a surgically exposed tibial plateau;

(c) positioning an elongated slope stylus member adjacent to the top of the surgically exposed tibial plateau, the elongated slope stylus member connected to the resection guide and extending along a plane substantially parallel to a plane defined by a guide surface of the resection guide, the slope stylus member serving as a reference for pivoting the guide block mount to adjust the slope of the guide surface;

(d) pivoting the guide block mount with respect to the base member so as to adjust the slope of a guide surface on the resection guide to approximate the anterior/posterior slope of the tibial plateau;

(e) fixing the guide surface of the resection guide in the desired position approximating the anterior/posterior slope of the tibial plateau;

(f) sliding the guide block mount relative to the base member along a depth adjustment axis extending substantially parallel to a longitudinal axis of the patient's tibia to a desired position in which the guide surface of the resection guide lies in a plane along which the tibia is to be resected to receive a tibial implant which will replace the natural articulating surfaces of the tibia; and (g) fixing the resection guide in the desired position along the depth adjustment axis.

13. The method of claim 12 further comprising the step of:

(a) positioning a depth stylus over the top of the surgically exposed tibial plateau with an end of the depth stylus at a point above the plane of the guide surface a distance equal to an implant depth, and wherein the step of sliding the guide block mount relative to the base member along the depth adjustment axis comprises sliding the guide block mount downwardly until the end of the depth stylus contacts the proximal surface of the tibia.

* * * * *

UNITED STATES PATENT AND TRADEMARK OFFICE
CERTIFICATE OF CORRECTION

PATENT NO. : 5,628,750

DATED : May 13, 1997

INVENTOR(S) : Whitlock, et al

It is certified that error appears in the above-identified patent and that said Letters Patent is hereby corrected as shown below:

Column 1, line 10, delete the word "resetted" and insert the word --resected--.

Column 4, line 40, delete the word "fight" and insert the word --right--.

Column 9, line 21, delete the word "slop" and insert the word --slope--.

Signed and Sealed this

Fifth Day of August, 1997

*Attest:*

BRUCE LEHMAN

*Attesting Officer*     *Commissioner of Patents and Trademarks*